United States Patent [19]

Jurd

[11] 4,357,344

[45] Nov. 2, 1982

[54] POLYBUTYLBENZYLPHENOLS AND BENZYL-3,4-METHYLENEDIOXYBENZENES IN INSECT POPULATION CONTROL

[75] Inventor: Leonard Jurd, Berkeley, Calif.

[73] Assignee: The United States of America as represented by the Secretary of Agriculture, Washington, D.C.

[21] Appl. No.: 25,132

[22] Filed: Mar. 29, 1979

[51] Int. Cl.³ .................. A01N 43/16; A01N 31/08
[52] U.S. Cl. .................................. 424/282; 424/346; 549/434; 549/435; 549/437; 549/445; 568/640; 568/744
[58] Field of Search ............... 260/340.5 R; 424/346, 424/282

[56] References Cited

U.S. PATENT DOCUMENTS

| | | | |
|---|---|---|---|
| 2,430,116 | 11/1947 | Holmes et al. | 260/340.5 R |
| 3,702,864 | 11/1972 | Kitamura et al. | 424/282 |
| 3,702,893 | 11/1972 | Fuchsman | 424/346 |
| 3,823,192 | 7/1974 | Holan et al. | 424/282 X |
| 3,839,586 | 10/1974 | Ludvik | 424/346 |
| 3,915,889 | 10/1975 | Jurd et al. | 424/346 |
| 3,920,846 | 11/1975 | Hanauye et al. | 424/346 |
| 3,993,782 | 11/1976 | Jurd | 424/346 |
| 4,029,818 | 6/1977 | Jurd et al. | 424/346 |

FOREIGN PATENT DOCUMENTS 2425713  1/1975  Fed. Rep. of Germany ...... 424/346

*Primary Examiner*—Ethel G. Love
*Attorney, Agent, or Firm*—M. Howard Silverstein; David G. McConnell; Margaret A. Connor

[57] ABSTRACT

Certain polybutylbenzylphenols and benzyl-3,4-methylenedioxybenzenes are useful for insect control especially as insect chemosterilants and oviposition inhibitors. The benzyl-3,4-methylenedioxybenzenes also find utility as growth inhibitors for mosquito larvae.

11 Claims, No Drawings

POLYBUTYLBENZYLPHENOLS AND BENZYL-3,4-METHYLENEDIOXYBENZENES IN INSECT POPULATION CONTROL

BACKGROUND OF THE INVENTION

1. Field of the Invention

This invention relates to and has among its objects the provision of novel organic compounds and the use thereof in insect control, particularly as anti-procreants. Further objects of the invention will be evident from the following description wherein parts and percentages are by weight unless otherwise specified. The symbol $\phi$ is used herein to represent the

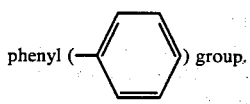

phenyl group.

2. Description of the Prior Art

Currently, there are various means for controlling insect populations. For example, one may apply an insecticide to insects or to their habitat. This method of control, however, has the disadvantage that the insecticide may cause harm to humans, animals, and useful insects (bees, for instance). Biological control of insects may be attained by employing compounds which serve as anti-procreants, i.e., chemosterilants or oviposition inhibitors. In the first type of biological control, a chemical (called a chemosterilant) is administered to the insects, which then become sexually sterile. The sexually sterilized insects mate with fertile insects, but the eggs laid do not yield any progeny. The result is a decrease in population of the insects. Another method of biological control involves administering a chemical (oviposition inhibitor) to the insects, with the result that the female species do not posit (lay) any eggs. Consequently, no progency are produced and a decrease in insect population is thus attained. Although the above means of biological control encompass two distinct ideas, the chemical compounds which produce the above effects may be termed generally as anti-procreants, that is, compounds which act either as chemosterilants and/or oviposition inhibitors and prevent procreation of the species.

The biological method of insect control offers many advantages over the usual method of applying an insecticide to insects or their habitat. For example, it avoids harm to humans, animals, and useful insects.

In controlling insects by sterilization or oviposition inhibition, a suitable compound is administered to a group of insects and these are then released in a locus where insects of the same species are present. As noted above, the treated insects mate with fertile ones but without producing progeny so that the overall population is decreased.

Insect anti-procreants are known and described in U.S. Pat. Nos. 3,959,489 ('489), 4,049,722 ('722), and 3,968,234 ('234). In '489 and '722 sexual sterility and oviposition in flies were inhibited by feeding the flies sufficient amounts of the following compounds:

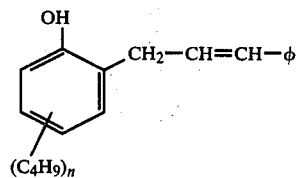

wherein n is 2 or 3.

Sexual sterility, but not oviposition inhibition, was obtained in '234 by employing compounds of the structure

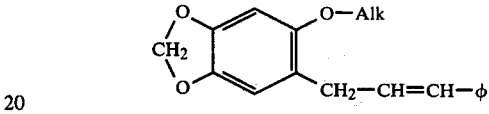

wherein Alk is an alkyl radical containing 1 to 4 carbon atoms.

Another means for controlling insect populations involves the use of compounds which inhibit the growth of the insect larvae. Such compounds are often referred to in the art as juvenile hormone mimics. These agents do not kill the larvae, but rather prevent the growth thereof beyond the larval or pupal stage. Consequently, the number of adults is substantially reduced. The juvenile hormone mimics actually cause several different situations, all of which result in controlling insect population. First of all, most of the treated larvae do not reach adulthood. Thus, the larvae survive for a period of time (possibly an entire growing season) as either larvae or pupae, and then die. During that period the larvae are, of course, very susceptible to predation and injurious climatic conditions. Furthermore, they are themselves incapable of reproduction, thus reducing the insect population for the next growing season. Secondly, some of the treated larvae may develop to various stages of adulthood. For example, the adult insect may only partially eclose, i.e., emerge from the larval or pupal shell. On the other hand, full eclosion may occur but the adult insect is either malformed or dead. In either case, the population of adult insects is substantially reduced.

The growth-inhibiting compounds have many advantages over insecticides and the like. First, the growth-inhibitors do not yield unwanted ecological side effects. Secondly, since the growth inhibitors act as juvenile hormone mimics, the insects do not develop a tolerance to the compounds. Thus, the compounds will not eventually become ineffective. Third, the growth-inhibiting compounds are not harmful to beneficial insects or mammals because they are quite specific for a particular kind of insect.

Larval growth-inhibiting compounds have been disclosed. For example, in Chemical Abstracts, Volume 80, No. 768 h (1974), and Mosquito News, Volume 31, No. 4, pp. 513–516 (1971), certain polybutylbenzyl phenols are offered as insecticides to control mosquitos. Generally, these compounds have the structure

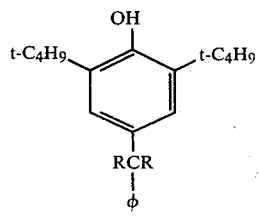

wherein R is independently hydrogen or methyl.

Finally, the following compound was described as a mosquito larvicidal agent in *Chemical Abstracts*, Volume 82, 125071 y (1975) and in German Offen. 2,425,713:

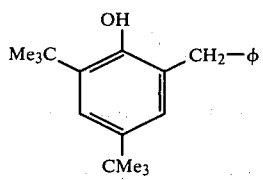

It should be noted that sexual sterility and oviposition inhibition, on the one hand, and larvicidal or juvenile hormone activity, on the other, although related generally because they are forms of insect population control, are different and unrelated concepts. In the former, insects exposed to the anti-procreant agents exhibit one or both of the following results: First, females may not posit any eggs. Second, even though eggs are posited, they do not hatch or otherwise further develop because the anti-procreant compound has induced sexual sterility in either the adult male or adult female or both. In any case, procreation is prevented.

Juvenile hormones are essential for growth and development of yound larvae. The last instar larvae are equipped with internal physiological mechanisms which interrupt the secretion of these juvenile hormones. The result is that larval growth and development are replaced by pupal and adult growth—a process generally known as metamorphosis. The metamorphic process can be thwarted by supplying the larvae with juvenile hormone or a juvenile hormone analogue before a certain critical period is reached. If this is done, partial or complete inhibition of metamorphosis is realized and adults either do not form or are misformed.

SUMMARY OF THE INVENTION

I have found that certain polybutylbenzylphenols and benzyl-3,4-methylenedioxybenzenes are useful in controlling insect population especially as insect anti-procreants. In addition, the benzyl-3,4-methylenedioxybenzenes serve as juvenile hormone mimics for mosquito larvae. The instant compounds have an activity equal to or greater than known compounds. Furthermore, by compounds apparently lack toxic and mutagenic properties possessed by many known insect anti-procreants and juvenile hormone mimics.

The compounds of the invention may be categorized as follows:

Group I. Polybutyl-2-benzyl phenols of the structure

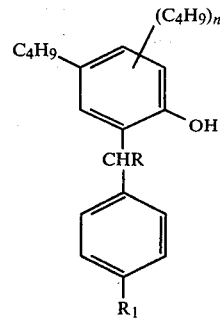

wherein
n is an integer from 1 to 3
R is hydrogen or lower alkyl containing from 1 to 6 carbon atoms
$R_1$ is hydrogen, lower alkyl containing from 1 to 6 carbon atoms, or lower alkoxy containing from 1 to 6 carbon atoms.

Group II. Polybutyl-4-benzyl phenols of the structure

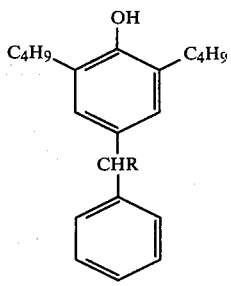

wherein R is hydrogen or lower alkyl containing from 1 to 6 carbon atoms.

Group III. Benzyl-3,4-methylenedioxybenzenes of the structure

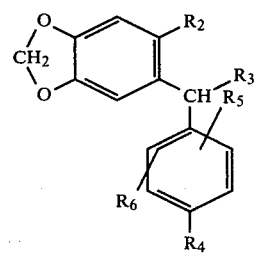

wherein
$R_2$ is hydrogen, lower alkyl containing from 1 to 6 carbon atoms, lower alkoxy containing from 1 to 6 carbon atoms, or lower alkenyl containing 2 to 6 carbon atoms,
$R_3$ is hydrogen or lower alkyl containing from 1 to 6 carbon atoms,
$R_4$, $R_5$ and $R_6$ are independently hydrogen, lower alkyl containing from 1 to 6 carbon atoms, and lower alkoxy containing from 1 to 6 carbon atoms and wherein, if $R_2$ is hydrogen, then $R_5$ and $R_6$ must be independently lower alkyl containing from 1 to 6 carbon atoms or lower alkoxy containing from 1 to 6 carbon atoms and wherein, if $R_4$, $R_5$, and $R_6$ are hydrogen and $R_3$ is methyl, then $R_2$ must be alkoxy containing 2–5 carbon atoms.

Group IV. 3,4-Methylenedioxybenzyl-3,4-methylenedioxybenzenes of the structure

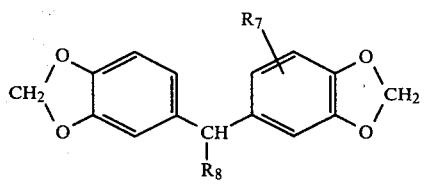

wherein
$R_7$ is lower alkyl containing 1 to 6 carbon atoms, lower alkoxy containing 2 to 6 carbon atoms, or lower alkenyl containing 2 to 6 carbon atoms, and
$R_8$ is hydrogen or lower alkyl containing from 1 to 6 carbon atoms.

The compounds of Groups III and IV are novel; the compounds of Group I wherein $R_1$ is other than hydrogen are also novel.

DESCRIPTION OF THE PREFERRED EMBODIMENTS

In one phase of the invention, insects are rendered either sexually sterile or, in the case of female insects, incapable of oviposition by administering to them any of the compounds heretofore described. The so-treated insects are then ready for release in insect breeding areas for mating with fertile insects of the same species. The administration of the compounds may be carried out by feeding the insects on a conventional insect food to which is added any of the aforesaid compounds in a concentration which is sufficient to induce either sexual sterility or oviposition inhibition in the insects, but is insufficient to kill them. The concentration required to achieve sterility or oviposition inhibition will vary depending on such factors as the kind of insect and the activity of the selected anti-procreant. It should be noted that the compounds of the invention are capable of acting as either a chemosterilant or an oviposition inhibitor depending on the particular concentration administered to the insects. As a chemosterilant the compounds are employed generally in a concentration of about 250 to 10,000 ppm; whereas about 500 to 10,000 ppm are necessary for oviposition inhibition. In any particular case the appropriate amount to use can readily be determined by pilot tests well-known to entomologists. The anti-procreants of the invention can be administered to captive insects in cages or other suitable containers. Alternatively, the anti-procreants may be administered to wild insects, for example, by making available to them feeding stations provided for ingestion by the insects with food admixed with any of the anti-procreants in either a sterilizing or an oviposition inhibiting proportion. Other methods of administering the instant compounds to insects will be evident to those skilled in the art and are included within the scope of my invention.

I have also discovered that the compounds of Groups III and IV are highly effective growth inhibitors for mosquito larvae. In accordance with this embodiment of my invention any one of these compounds is applied in a growth-inhibiting amount to the habitat or breeding place of the mosquito larvae, e.g., added to the water wherein the larvae are present. As a result, the growth of the mosquito larvae beyond the larval or pupal stage is inhibited so that few, if any, adult mosquitos are formed. The concentration of the compound required to achieve growth inhibition will vary depending on the activity of the selected compound. In any particular case the appropriate amount to use can readily be determined by pilot tests well-known to entomologists. In many cases good results have been attained where the compounds are applied in a concentration of about 0.01 to 1 ppm in bodies of water where the mosquito larvae exist. The growth inhibitors of the invention are effective only on mosquito larvae; they have no effect on adult mosquitoes and consequently must be administered to the larvae to attain the desired result of growth inhibition.

Because the compounds of the invention are effective in very minor concentrations, it is preferred that they be dissolved or suspended in a carrier prior to application to the breeding centers. The solution or suspension increases the bulk, and thus makes it easy to administer small amounts of the compounds to the mosquito breeding area. Solvents appropriate for this purpose should be volatile ones, such as acetone, ethyl ether, ethanol, benzene, xylene, petroleum naphtha, and the like.

It is within the compass of the invention to use a single compound as herein described or mixtures of two or more of these compounds.

Typical examples of compounds which may be used in the method of the invention are the following:

Group I: 4,6-di-t-butyl-2-benzyl phenol; 4,6-di-t-butyl-2-(α-alkylbenzyl) phenols, wherein the α-alkyl group is methyl, ethyl, propyl, butyl, pentyl, and hexyl, respectively; 4,6-di-t-butyl-2-(4-alkoxybenzyl) phenols, wherein the 4-alkoxy group is methoxy, ethoxy, propoxy, butoxy, pentoxy, and hexoxy, respectively; 4,6-di-t-butyl-2-(4-alkylbenzyl) phenols wherein the 4-alkyl group is methyl, ethyl, propyl, butyl, pentyl, hexyl, respectively; 4,6-di-t-butyl-2-(4-alkoxy-α-alkylbenzyl) phenols, wherein the 4-alkoxy and the α-alkyl groups are those listed above; and 4,6-di-t-butyl-2-(4-alkyl-α-alkylbenzyl) phenols wherein the 4-alkyl and the α-alkyl groups are those listed above.

Group II: 2,6-di-t-butyl-4-(α-alkylbenzyl) phenols wherein the α-alkyl group is methyl, ethyl, propyl, butyl, pentyl, and hexyl.

Group III: (4-alkoxybenzyl)-3,4-methylenedioxy-6-alkoxybenzenes wherein the 6-alkoxy group and the 4-alkoxy group are independently methoxy, ethoxy, propoxy, butoxy, pentoxy, and hexoxy, isopropoxy, t-butoxy, iso-butoxy, t-amyloxy, isopentoxy, isohexoxy; (α-methyl-4-alkoxybenzyl)-3,4-methylene-dioxy-6-alkoxybenzenes wherein the 6-alkoxy group and the 4-alkoxy group are those listed above, and the α-alkyl group is methyl, ethyl, propyl, butyl, pentyl, or hexyl; (α-methylbenzyl)-3,4-methylenedioxy-6-alkoxybenzenes wherein the α-methyl group is from the above-listed alkyl groups and the 6-alkoxy group is ethoxy, propoxy, butoxy, or pentoxy; (4-alkoxybenzyl)-3,4-methylenedioxy-6-alkenylbenzenes wherein the 6-alkenyl group is ethenyl, propenyl, butenyl, pentenyl, or hexenyl and the 4-alkoxy group is one of the aforementioned; (4-alkoxybenzyl)-3,4-methylenedioxy-6-alkylbenzenes wherein the 6-alkyl group is methyl, ethyl, propyl, butyl, pentyl, or hexyl; (3-alkyl-4-alkoxybenzyl)-3,4-methylenedioxybenzenes wherein the 4-alkoxy group is selected from the group listed above and the 3-alkyl group is methyl, ethyl, propyl, butyl, pentyl, or hexyl, (3,5-dialkyl-4-alkoxybenzyl)-3,4-methylenedioxybenzenes wherein the 4-alkoxy group is one of those listed above and the 3,5-dialkyl groups are independently methyl, ethyl, propyl, butyl, pentyl, or hexyl; (2,4-dialkoxybenzyl)-3,4-methylenedioxybenzenes wherein the 2,4-dialkoxy groups are independently methoxy, ethoxy, propoxy, butoxy, pentoxy, or hexoxy; (2-methyl-4-alkoxy-5-isopropylbenzyl)-3,4-methylenedioxybenzenes wherein the 4-alkoxy group is methoxy or n-propoxy.

Group IV: (6-Alkoxy-3,4-methylenedioxybenzyl)-3,4-methylene dioxybenzenes wherein the 6-alkoxy group is methoxy, ethoxy, propoxy, butoxy, pentoxy, or hexoxy; (α-alkyl-6-alkoxy-3,4-methylenedioxybenzyl)-3,4-methylenedioxy-benzenes wherein the α-alkyl group is methyl, ethyl, propyl, butyl, pentyl, or hexyl, and the 6-alkoxy group is selected from the aforementioned group.

The compounds of Groups I and II, except where either R or R₁ is hydrogen but not both, may be prepared by refluxing a mixture of the appropriate polybutyl phenol with the appropriate alcohol in an aqueous acid medium. For example, 4,6-di-t-butyl-2-benzylphenols can be prepared by reacting 2,4-di-t-butylphenol with the appropriate alcohol under reflux in the presence of aqueous formic acid. This synthesis is illustrated by the following formulas

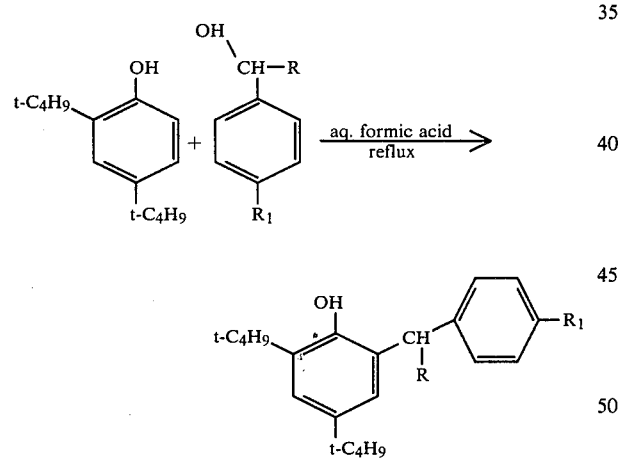

wherein R and R₁ are defined as described above. To prepare 2,6-di-butyl-4-benzyl phenols one proceeds as follows:

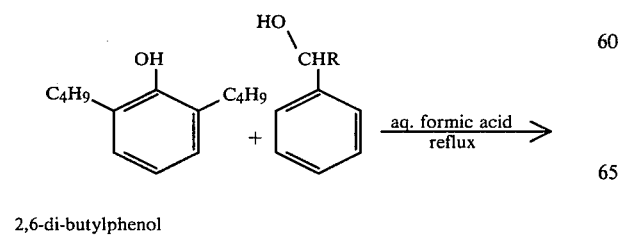

2,6-di-butylphenol

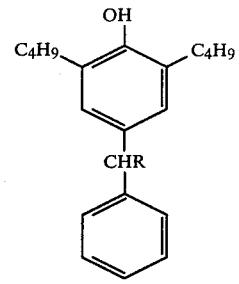

wherein R is defined as described above.

The remaining compounds of Groups I and II can be synthesized by appropriate condensation reactions such as the Friedel-Crafts reaction and the like.

Similarly, most of the compounds of Groups III and IV can be prepared by condensation of 3,4-methylenedioxyphenol with the appropriate alcohol in an aqueous acidic medium and then formation of an alkyl ether. Schematically, the reaction may be represented as follows:

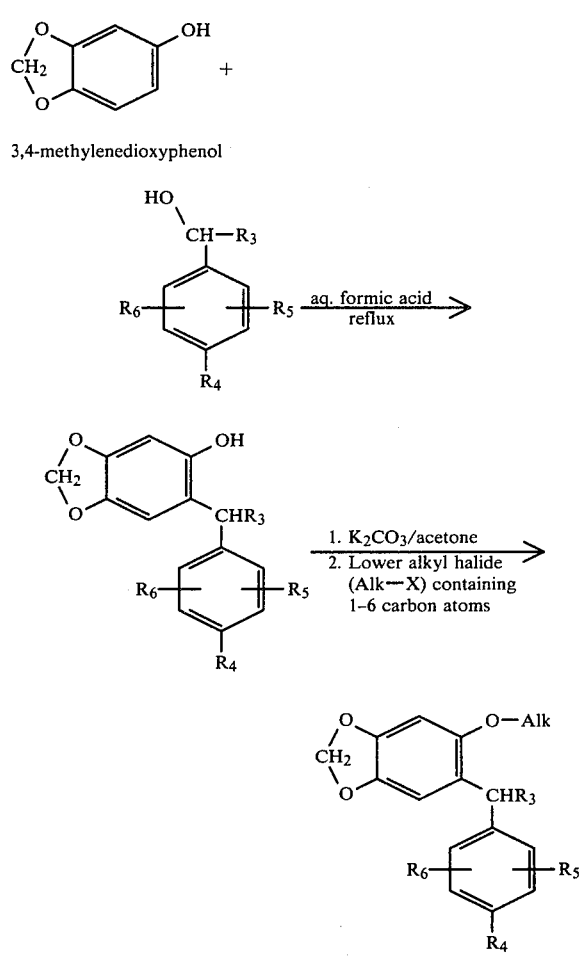

wherein R₃ to R₆ are defined as above.

Some of the Group III compounds are prepared by reaction of the appropriate lower alkenyl-substituted 3,4-methylenedioxybenzene and the appropriate alcohol.

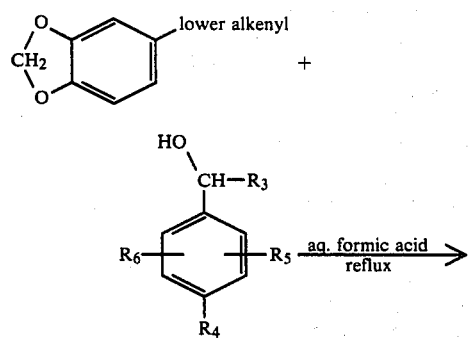

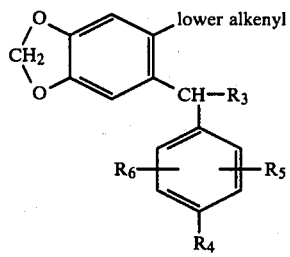

wherein the lower alkenyl group contains from 2 to 6 carbon atoms and $R_3$ to $R_6$ are defined as described hereinabove.

Similarly compounds of Group IV wherein $R_7$ is lower alkyl or alkenyl can be prepared from a lower alkyl- or alkenyl-substituted 3,4-methylenedioxybenzene and an appropriate alcohol.

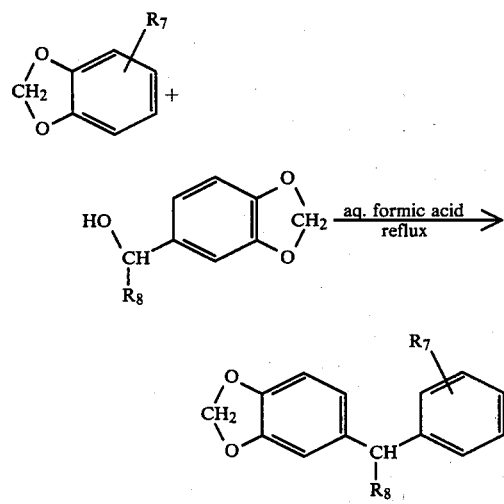

To prepare the compounds of Group IV wherein $R_7$ is lower alkoxy 3,4-methylenedioxyphenol is condensed with a substituted α-hydroxymethyl-3,4-methylenedioxyphenol followed by alkylation to form the alkyl ether.

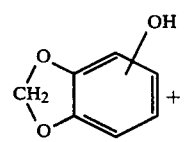

3,4-methylenedioxyphenol

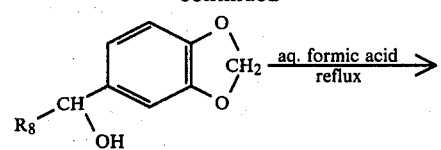

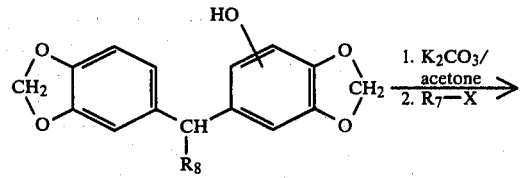

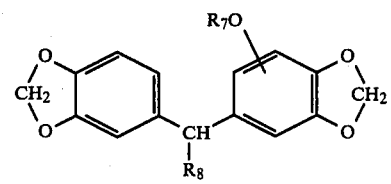

Another aspect of my invention concerns a novel synthesis of the Group I compounds. I have found that these compounds can be prepared by simply admixing the appropriate polybutylphenol with the appropriate alcohol and heating the mixture for a period of about 0.5 to 2.0 hours. The temperature of the reaction is about 170° to 220° C. Generally, about 0.5 to 1.0 parts of alcohol are used per part of polybutylphenol. The resulting product is recovered from the reaction mixture by conventional techniques including fractional distillation and crystallization from solvents.

The above-described synthetic procedure avoids the cumbersome steps encountered when an aqueous acidic medium is employed. Furthermore, the yields of the final product in both synthetic approaches are comparable.

The following schematic representation illustrates my novel synthetic approach by way of example:

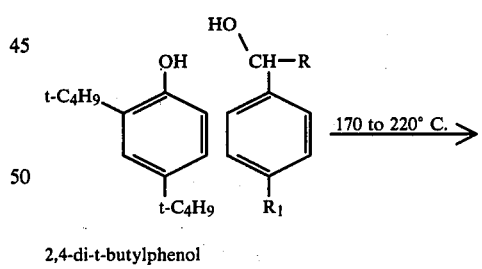

2,4-di-t-butylphenol

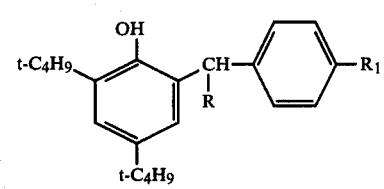

wherein R and $R_1$ are defined as described above.

It should be noted that my novel synthesis for the preparation of the compounds of Group I cannot be employed to prepare the compounds of Group II. The compounds of Groups III and IV can be synthesized as described above if a small amount, 0.05 to 0.5%, of a weak acid such as citric acid, oxalic acid, hypophosphorous acid, and so forth is added to the reaction mixture.

The activity of the compounds of Groups I to IV is unexpected and not shared by closely-related compounds. For example, the following compounds are ineffective in my method: 2-benzyl-4-t-butylphenol, 2-(α-methylbenzyl)-4-t-butylphenol, 4-(α,α-dimethylbenzyl)-2,6-di-t-butylphenol, 4-(α-methyl-4-methoxybenzyl)-2,6-di-t-butylphenol, 4-methoxybenzyl-2,6-di-t-butylphenol, α-vinylbenzyl-3,4-methylenedioxy-6-alkoxybenzenes wherein the 6-alkoxy group is allyloxy, methoxy, ethoxy, n-propoxy, 6-(4-methoxybenzyl)-3,4-methylenedioxyphenol, α-methylbenzyl-3,4-methylenedioxy-6-methoxybenzene, α,α-dimethylbenzyl-3,4-methylenedioxy-6-alkoxybenzenes wherein the 6-alkoxy group is methoxy, ethoxy, propoxy, butoxy, or pentoxy, α-methylbenzyl-3,4-methylenedioxy-6-alkoxybenzenes wherein the 6-alkoxy group is methoxy or hexoxy, 3-alkyl-4-hydroxybenzyl-3,4-methylenedioxybenzenes wherein the 3-alkyl group is methyl or t-butyl, 2-hydroxy-5-alkylbenzyl-3,4-methylenedioxybenzenes wherein the 5-alkyl group is methyl or ethyl, 4-hydroxybenzyl-3,4-methylenedioxybenzene.

The compounds of the invention are especially effective as anti-procreants for flies or the order Diptera including, but not limited to, the following families: Muscidae (housefly), Calliphoridae (screw-worm fly, blowfly, cluster fly), Tipulidae, Psychodidae, Culicidae, Blepharoceridae, Anisopidae, Cecidomyiidae, Bibionidae, Mycetophilidae, Simuliidae, Dixidae, Chironomidae, Mydaidae, Asilidae, Bombyliidae, Tabanidae, Stratiomyidae, Coenomyidae, Phoridae, Acroceridae, Nemestrinidae, Rhagionidae, Lonchopteridae, Dolichopodidae, Syrphidae, Asilidae, Scenopinidae, Apioceridae, Therevidae, Pipunculidae, Conopidae, Platypezidae, Empididae, Tachinidae, Sarcophagidae, Psilidae, Anthomyiidae, Gasterophilidae, Sepsidae, Helomyzidae, Tanypezidae, Canopidae, Ortalidae, Sciomyzidae, Sapromyzidae, Diposidae, Trypetidae, Borboridae, Ephydridae, Chloropodiae, Drosophilidae, Agromyzidae, Psilidae, Nycteribiidae, Streblidae, Hippoboscidae, and so forth.

EXAMPLES

The invention is further demonstrated by the following illustrative examples. Temperatures are in degrees Centigrade unless otherwise indicated.

EXAMPLE 1

Synthesis of Group I Compounds

A. 4,6-Di-t-butyl-2-α-methylbenzylphenol: A solution of 2,4-di-t-butylphenol (51 g) and 1-phenylethanol (31 g) in 40 ml of acetic acid and 80 ml of formic acid was refluxed for 6 hours and then diluted with 200 ml of water. The product was distilled giving 71.5 g of a colorless oil, b.p. 157°–158° at 2 mm Hg. The molecular weight (mass) of the product as determined by mass spectrometry was 310.2308; calculated for $C_{22}H_{30}O = 310.2296$. The proton magnetic resonance (pmr) spectrum of this compound at 100 MHz in deuterated chloroform ($CDCl_3$) exhibited absorbances as follows: δ1.34, 9 protons (H), singlet (S); δ1.55, 9H, S; δ1.65, 3H, doublet (D) (J=7.5 Hz); δ4.22, 1H, quartet (Q) (J=7.5 Hz); δ4.53, 1H, S; δ7.20, 7H, multiplet (M).

B. Similarly, 4,6-di-t-butyl-2-(α-methyl-4-methoxybenzyl)phenol was prepared from 2,4-di-t-butylphenol and α-methyl-4-methoxybenzyl alcohol. A yellow oil (b.p. 180° at 1.0 mm Hg) which crystallized was obtained. The product was recrystallized from methanol to give colorless needles melting at room temperature (Found: C, 81.0; H, 9.45 Calc. for $C_{23}H_{32}O_2$: C, 81.1; H, 8.47%). The pmr spectrum determined as above exhibited the following: δ1.35, 9H, S; δ1.37, 9H, S; δ1.63, 3H, D (J=7 Hz); δ3.78, 3H, S; δ4.17, Q, 1H (J=7 Hz); δ4.62, 1H, S; δ6.84, 2H, D (J=8 Hz); δ7.10-7.30, 4H, M.

C. 4,6-Di-t-butyl-2-(4-methoxybenzyl)phenol was prepared as follows: A solution of 2,4-di-t-butylphenol (57.5 g), 4-methoxybenzyl alcohol (34.5 g) and oxalic acid (2 g) in acetic acid (80 ml) and water (2 ml) was refluxed for 7 hours, diluted with water, and extracted with chloroform. Distillation of the chloroform extract gave an oil (b.p. 200°–210° C. at 2 mm Hg) which crystallized (58 g; 71.4%). The product was recrystallized from methanol to give glistening colorless needles, m.p. 84°–85° (Found: C, 81.0; H, 8.21. Calc. for $C_{22}H_{30}O_2$: C, 80.9; H, 9.26%). The pmr spectrum exhibited the following: δ1.30, 9H, S; δ1.38, 9H, S; δ3.79, 3H, S; δ3.83, 2H, S; δ4.62, 1H, S; δ6.84, 2H, D (J=8 Hz); δ7.02, 1H, D (J=2 Hz); δ7.14, 2H, D (J=8 Hz); δ7.23, 1H, D (J=Hz).

D. 2,4-Di-t-butyl-6-benzylphenol was prepared according to the method disclosed by H. A. Green, U.S. Pat. No. 3,193,526.

EXAMPLE 2

Synthesis of Group II Compounds

E. 2,6-Di-t-butyl-4-(α-methylbenzyl)phenol was prepared by refluxing 2,6-di-t-butylphenol (51 g) and 1-phenylethanol (31 g) in acetic acid (40 ml) and formic acid (75 ml) as described for A. The product was obtained as a colorless oil, b.p. 166°–168° at 1.0 mm Hg (62 g); (meas. mass=310.2309. Calc. for $C_{22}H_{30}O=310.2296$). The pmr spectrum was: δ1.40, 18H, S; δ1.61, 3H, D (J=8 Hz); δ4.06, 1H, Q (J=8 Hz); δ5.02, 1H, S; δ7.01, 2H, S; δ7.22, 5H, S.

F. 2,6-Di-t-butyl-4-(4-methoxybenzyl)phenol was prepared as described for A above. A mixture of 2,6-di-t-butylphenol (51.5 g), 4-methoxybenzyl alcohol (34.5 g), formic acid (100 ml) and acetic acid (100 ml) was refluxed for 5 hours, diluted with water, and extracted with chloroform. Evaporation of the chloroform gave an oil which crystallized. Recrystallization from methanol gave colorless needles, mp 139° (58 g) (Found: C, 80.7; H, 9.30. Calc. for $C_{22}H_{30}O_2$: C, 80.9; H, 9.26%); pmr spectrum: δ1.42, 18H, S; δ3.79, 3H, S; δ3.86, 2H, S; δ5.04, 1H, S; δ6.83, 2H, D (J=8 Hz); δ6.98, 2H, S; δ7.12, 2H, D (J=8 Hz).

G. 2,6-Di-t-butyl-4-(α-methyl-4-methoxybenzyl)phenol: Condensation of 2,6-di-t-butylphenol (80 g) and α-methyl-4-methoxybenzyl alcohol (40 g) in acetic-formic acid solution as described for E above gave, on distillation of the product, a colorless oil, b.p. 192°–201° at 2.0 mm Hg (74 g). The oil crystallized from methanol to give glistening colorless needles, m.p. 83°–84° (49 g) (Found: C, 81.1; H, 9.42. Calc. for $C_{23}H_{32}O_2$: C, 81.1; H, 9.47%); pmr spectrum: δ1.42, 18H, S; δ1.59, 3H, D (J=7.5 Hz); δ3.77, 3H, S; δ4.03, 1H, Q (J=7.5 Hz); δ5.02, 1H, S; δ6.81, 2H, D (J=8.5 Hz); δ7.01, 2H, S; δ7.14, 2H, D (J=8.5 Hz).

EXAMPLE 3

Synthesis of Group III Compounds

H. (α-Methyl-4-methoxybenzyl)-3,4-methylenedioxy-6-methoxybenzene was prepared according to the following procedure: A solution of sesamol (27.6 g, 0.2 mole), 1-(4-methoxyphenyl)ethanol (30.4 g, 0.2 mole), and oxalic acid (2 g) in glacial acetic acid (60 ml) and water (10 ml) was refluxed for 7 hours, diluted with water, and extracted with ether. Distillation of the ether extract gave an oil, b.p. 235°–237° at 5 mm Hg (53 g), which crystallized from benzene-skelly solve F to yield glistening, colorless needles, m.p. 93°–94° (Found: C, 70.5; H, 5.86. Calc. for $C_{16}H_{16}O_4$: C, 70.6; H, 5.92%); pmr spectrum: $\delta 1.53$, 3H, D (J=7 Hz); $\delta 3.77$, 3H, S; $\delta 4.21$, 1H, Q (J=7 Hz); $\delta 4.58$, 1H (OH), S; $\delta 5.86$, 2H, S; $\delta 6.35$, 1H, S; $\delta 6.70$, 1H, S; $\delta 6.81$, 2H, D (J=9 Hz); $\delta 7.17$, 2H, D (J=9 Hz).

The above product was alkylated by refluxing its solution in acetone (13.6 g in 50 ml) with potassium carbonate (25 g) and excess (2 mol. equivs.) of methyl iodide for 20 hours. The reaction mixture was diluted with 5% aqueous sodium hydroxide (100 ml) and extracted with ether. Distillation gave a colorless oil, b.p. 184° at 1.0 mm Hg (Found: C, 71.4; H, 6.41. Calc. for $C_{17}H_{18}O_4$: C, 71.3; H, 6.34%); pmr spectrum: $\delta 1.49$, 3H, D (J=7 Hz); $\delta 3.69$, 3H, S; $\delta 3.74$, 3H, S; $\delta 4.46$, 1H, Q (J=7 Hz); $\delta 5.82$, 2H, S; $\delta 6.48$, 1H, S; $\delta 6.62$, 1H, S; $\delta 6.78$, 2H, D (J=9 Hz); $\delta 7.03$, 2H, D (J=9 Hz).

I. (α-Methyl-4-methoxybenzyl)-3,4-methylenedioxy-6-n-propoxybenzene was prepared by the procedure in H above and exhibited the following properties: colorless oil, b.p. 191°–192° at 1.0 mm Hg, which rapidly crystallized (13.1 g). Recrystallization from methanol gave colorless needles, m.p. 84° (Found: C, 72.4; H, 7.09. Calc. for $C_{19}H_{22}O_4$: C, 72.6; H, 7.05%); pmr spectrum: $\delta 0.97$, 3H, triplet (T) (J=7 Hz); $\delta 1.50$, 3H, D (J=7 Hz); $\delta 1.70$, 2H, M, (J=7 Hz); $\delta 3.73$, 3H, S; $\delta 3.78$, 2H, M; $\delta 4.49$, 1H, Q (J=7 Hz); $\delta 5.81$, 2H, S; $\delta 6.46$, 1H, S; $\delta 6.64$, 1H, S; $\delta 6.78$, 2H, D (J=9 Hz); $\delta 7.13$, 2H, D (J=9 Hz).

J. Similarly (to H and I), (α-methyl-4-methoxybenzyl)-3,4-methylenedioxy-6-n-butoxybenzene was prepared as a colorless oil, b.p. 202°–203° at 1.5 mm Hg (Found: C, 73,4; H, 7.38. Calc. for $C_{20}H_{24}O_4$: C, 73.1; H, 7.37%); pmr spectrum: $\delta 0.93$, 3H, T (J=7 Hz); $\delta 1.48$, 3h, D (J=8 Hz); $\delta 1.55$, 4H, M; $\delta 3.76$, 3H, S; $\delta 3.80$, Q (J=7 Hz); $\delta 4.48$, 1H, Q (J=8 Hz); $\delta 5.83$, 2H, S; $\delta 6.47$, 1H, S; $\delta 6.63$, 1H, S; $\delta 6.78$, 2H, D (J=9 Hz); $\delta 7.12$, 2H, D (J=9 Hz).

K. In the same way, (α-methyl-4-methoxybenzyl)-3,4-methylenedioxy-6-n-pentoxybenzene was obtained as a yellow oil, b.p. 183°–200° C. at 5 mm Hg.

L. (4-Methoxybenzyl)-3,4-methylenedioxy-6-methoxybenzene was prepared from 6-(4-methoxybenzyl)-3,4-methylenedioxyphenol (L. Jurd, Tetrahedron, Vol. 33, pp. 163–168 (1977) by methylation as described above in H. Colorless prisms were obtained from benzene-solve F, m.p. 56°–57° (Found: C, 70.5; H, 5.95. Calc. for $C_{16}H_{16}O_4$: C, 70.6; H, 5.92%); pmr spectrum: $\delta 3.74$, 3H, S; $\delta 3.77$, 3H, S; $\delta 3.82$, 2H, S; $\delta 5.85$, 2H, S; $\delta 6.52$, 1H, S; $\delta 6.55$, 1H, S; $\delta 6.80$, 2H, D (J=9 Hz); $\delta 7.11$, 2H, D (J=9 Hz).

The following compounds (L through R) were prepared by the procedure used in K.

M. (4-Methoxybenzyl)-3,4-methylenedioxy-6-ethoxybenzene, slightly yellow oil, b.p. 178°–180° at 0.5 mm Hg (Found: C, 71.6; H, 6.38. Calc. for $C_{17}H_{18}O_4$: C, 71.3; H, 6.34%); pmr spectrum: $\delta 1.34$, 3H, T (J=7 Hz); $\delta 3.76$, 3H, S; $\delta 3.82$, 2H, S; $\delta 3.93$, 2H, Q (J=7 Hz); $\delta 5.84$, 2H, S; $\delta 6.49$, 1H, S; $\delta 6.56$, 1H, S; $\delta 6.79$, 2H, D (J=9 Hz); $\delta 7.10$, 2H, D (J=9 Hz).

N. (4-Methoxybenzyl)-3,4-methylenedioxy-6n-propoxybenzene, colorless oil, b.p. 183°–184° at 0.5 mm Hg (Found: C, 71.9; H, 6.64. Calc. for $C_{18}H_{20}O_4$: C, 72.0; H, 6.71%); pmr spectrum: $\delta 1.00$, 3H, T (J=7 Hz); $\delta 1.76$, 2H, M; $\delta 3.77$, 3H, S; $\delta 3.83$, 4H, M; $\delta 5.82$, 2H, S; $\delta 6.49$, 1H, S; $\delta 6.56$, 1H, S; $\delta 6.78$, 2H, D (J=9 Hz); $\delta 7.01$, 2H, D (J=9 Hz).

O. (4-Methoxybenzyl)-3,4-methylenedioxy-6-isopropoxybenzene, colorless oil, b.p. 176°–178° at 0.5 mm Hg (Found: C, 71.9; H, 6.64. Calc. for $C_{18}H_{20}O_4$: C, 72.0; H, 6.71%); pmr spectrum: $\delta 1.24$, 6H, D (J=6 Hz); $\delta 3.76$, 3H, S; $\delta 3.81$, 2H, S; $\delta 4.37$, 1H, M (J=6 Hz); $\delta 5.84$, 2H, S; $\delta 6.51$, 1H, S; $\delta 6.55$, 1H, S; $\delta 6.79$, 2H, D (J=9 Hz); $\delta 7.11$, 2H, D (J=9 Hz).

P. (4-Methoxybenzyl)-3,4-methylenedioxy-6-n-butoxybenzene, colorless oil, b.p. 192°–193° at 0.5 mm Hg (Found: C, 72.8; H, 7.09. Calc. for $C_{19}H_{22}O_4$: C, 72.6; H, 7.05%); pmr spectrum: $\delta 0.94$, 3H, T (J=7 Hz); $\delta 1.54$, 4H, M; $\delta 3.76$, 3H, S; $\delta 3.84$, 4H, M; $\delta 5.84$, 2H, S; $\delta 6.49$, 1H, S; $\delta 6.55$, 1H, S; $\delta 6.78$, 2H, D (J=9 Hz); $\delta 7.10$, 2H, D (J=9 Hz).

Q. (4-Methoxybenzyl)-3,4-methylenedioxy-6-isobutoxybenzene, colorless oil, b.p. 184°–186° at 0.5 mm Hg (Found: C, 72.5; H, 7.00. Calc. for $C_{19}H_{22}O_4$: C, 72.6; H, 7.05%); pmr spectrum: $\delta 0.98$, 6H, D (J=6 Hz); $\delta 2.02$, 1H, M; $\delta 3.74$, 7H, M; $\delta 5.81$, 2H, S; $\delta 6.48$, 1H, S; $\delta 6.56$, 1H, S; $\delta 6.78$, 2H, D (J=9 Hz); $\delta 7.10$, 2H, D (J=9 Hz).

R. (4-Methoxybenzyl)-3,4-ethylenedioxy-6-n-pentoxybenzene, colorless oil, b.p. 194°–195° at 0.5 mm Hg (Found: C, 73.1; H, 7.42. Calc. for $C_{20}H_{24}O_4$: C, 73.1, H, 7.37%); pmr spectrum: $\delta 0.90$, 3H, T (J=6 Hz); $\delta 1.36$, 4H, M; $\delta 1.72$, 2H, M; $\delta 3.75$, 3H, S; $\delta 3.85$, 4H, M; $\delta 5.83$, 2H, S; $\delta 6.48$, 1H, S; $\delta 6.55$, 1H, S; $\delta 6.78$, 2H, D (J=9 Hz); $\delta 7.10$, 2H, D (J=9 Hz).

S. (4-Methoxybenzyl)-3,4-methylenedioxy-6-iso-pentoxybenzene, colorless oil, b.p. 193° at 0.5 mm Hg (Found: C, 73.2; H, 7.40. Calc. for $C_{20}H_{24}O_4$: C, 73.1; H, 7.3%); pmr spectrum: $\delta 0.92$, 6H, D (J=6 Hz); $\delta 1.68$, 3H, M; $\delta 3.76$, 3H, S; $\delta 3.84$, 4H, M; $\delta 5.82$, 2H, S; $\delta 6.49$, 1H, S; $\delta 6.56$, 1H, S; $\delta 6.78$, 2H, D (J=9 Hz); $\delta 7.08$, 2H, D (J=9 Hz).

T. (α-Methylbenzyl)-3,4-methylenedioxy-6-methoxybenzene was prepared as follows: A solution of sesamol (41.4 g), 1-phenylethyl alcohol (36.6 g) and oxalic acid (2 g) in acetic acid (100 ml) and water (10 ml) was refluxed for 24 hours and diluted with water. Distillation of the oily product gave a pale yellow oil, b.p. 204°–205° at 4.0 mm Hg (56 g) which crystallized. Recrystallization from benzene-skelly solve F gave (α-methylbenzyl)-3,4-methylenedioxy-6-hydroxybenzene as colorless needles, m.p. 101°–102° (Found: C, 74.2, H, 5.75. Calc. for $C_{15}H_{14}O_3$: C, 74.4; H, 5.83%); pmr spectrum: $\delta 1.57$, 3H, D (J=7 Hz); $\delta 4.29$, 1H, Q (J=7 Hz); $\delta 4.50$, 1H, S; $\delta 5.86$, 2H, S; $\delta 6.35$, 1H, S; $\delta 6.72$, 1H, S; $\delta 7.25$, 5H, S.

The above product was methylated as described above in H yielding a colorless oil, b.p. 176° at 3.0 mm Hg (Found: C, 75.0; H, 6.37. Calc. for $C_{16}H_{16}O_3$: C, 75.0; H, 6.29%); pmr spectrum: $\delta 1.52$, 3H, D (J=7 Hz); $\delta 3.66$, 3H, S; $\delta 4.52$, 1H, Q (J=7 Hz); $\delta 5.82$, 2H, S; $\delta 6.49$, 1H, S; $\delta 6.65$, 1H, S; 7.22, 5H, S.

Similarly, compounds U through W were prepared.

U. (α-Methylbenzyl)-3,4-methylenedioxy-6-n-propoxybenzene, colorless prisms from methanol, m.p. 63° (Found: C, 76.2; H, 7.15. Calc. for $C_{18}H_{20}O_3$: C, 76.0, H, 7.09%); pmr spectrum: $\delta 0.96$, 3H, T (J=7 Hz); $\delta 1.52$, 3H, D (J=7 Hz); $\delta 1.72$, 2H, M (J=7 Hz); $\delta 3.79$, 2H, T (J=7 Hz); δ4.53, 1H, Q (J=7 Hz); δ5.81, 2H, S; δ6.46, 1H, S; δ6.67, 1H, S; δ7.20, 5H, S.

V. (α-Methylbenzyl)-3,4-methylenedioxy-6-n-butoxybenzene, colorless needles from methanol, m.p. 43° (Found: C, 76.3; H, 7.47. Calc. for $C_{19}H_{22}O_3$: C, 76.5; H, 7.43%); pmr spectrum: δ0.92, 3H, T (J=7 Hz); δ1.52, 3H, D (J=7 Hz); δ1.55, 4H, M; δ3.82, 2H, T (J=7 Hz); δ4.52, 1H, Q (J=7 Hz); δ5.84, 2H, S; δ6.48, 1h, S; δ6.67, 1H, S; δ7.21, 5H, M.

W. (α-Methylbenzyl)-3,4-methylenedioxy-6-n-pentoxybenzene, colorless plates from methanol, m.p. 46°-47° (Found: C, 76.7; H, 7.80. Calc. for $C_{20}H_{24}O_3$: C, 76.9; H, 7.74%); pmr spectrum: δ0.90, 3H, T (J=6 Hz); δ1.35, 4H, M; δ1.53, 3H, D (J=7 Hz); δ1.64, 2H, M; δ3.80, 2H, T (J=6 Hz); δ4.51, 1H, Q (J=7 Hz); δ5.82, 2H, S; δ6.46, 1H, S; δ6.67, 2H, S; δ7.20, 5H, S.

X. (α,α-Dimethylbenzyl)-3,4-methylenedioxy-6-methoxybenzene was prepared as follows: A mixture of sesamol (44 g), α,α-dimethylbenzyl alcohol (44 g), oxalic acid (3g), acetic acid (100 ml) and water (10 ml) was refluxed for 2.5 hours, diluted with water and extracted with chloroform. Distillation of the chloroform extract gave an oil, b.p. 160°-163° at 0.5 mm Hg (60 g) which crystallized from aqueous methanol to give colorless needles, m.p. 75°-76° (Found: C, 75.0; H, 6.26. Calc. for $C_{16}H_{16}O_3$: C, 75.0; H, 6.29%); pmr spectrum: δ1.63, 6H, S; 4.12, 1H, S; δ5.81, 2H, S; δ6.33, 1H, S; δ6.98, 1H, S; δ6.31, 5H, S.

In a similar manner, the compounds Y-BB were prepared.

Y. (α,α-Dimethylbenzyl)-3,4-methylenedioxy-6-ethoxybenzene, colorless needles, m.p. 78°-79° (Found: C, 75.9; H, 7.15. Calc. for $C_{18}H_{20}O_3$: C, 76.0, H, 7.09%); pmr spectrum: δ0.79, 3H, T (J=7 Hz); δ1.63, 6H, S; δ3.44, 2H, Q (J=7 Hz); δ5.90, 2H, S; δ6.42, 1H, S; δ7.02, 1H, S; δ7.17, 5H, S.

Z. (α,α-Dimethylbenzyl)-3,4-methylenedioxy-6-n-propoxybenzene, colorless plates, from methanol, m.p. 94° (Found: C, 76.4; H, 7.42. Calc. for $C_{19}H_{22}O_3$: C, 76.5; H, 7.43%); pmr spectrum: δ0.67, 3H, T (J=7 Hz); δ1.19, 2H, M; δ1.64, 6H, S; δ3.37, 2H, T (J=7 Hz); δ5.91, 2H, S; δ6.43, 1H, S; δ7.23, 1H, S; δ7.36, 5H, S.

AA (α, α-Dimethylbenzyl)-3,4-methylenedioxy-6-n-butoxybenzene, colorless plates, from methanol, m.p. 89° (Found: C, 76.8, H, 7.67. Calc. for $C_{20}H_{24}O_3$: C, 76.9; H, 7.74%); pmr spectrum: δ0.74, 3H, T (J=6 Hz); δ1.10, 4H, M; δ1.62, 6H, S; δ3.39, 2H, T (J=6 Hz); δ5.88, 2H, S; δ6.41, 1H, S; δ7.02, 1H, S; δ7.15, 5H, S.

BB. (α,α-Dimethylbenzyl)-3,4-methylenedioxy-6-n-pentoxybenzene, colorless, flat needles from methanol, m.p. 55°-56° (Found: C, 77.3; H, 8.01. Calc. for $C_{21}H_{26}O_3$: C, 77.3; H, 7.66%); pmr spectrum: δ0.82, 3H, T (J=7 Hz); δ1.32, 6H, M; δ1.62, 6H, S; δ3.42, 2H, T (J=7 Hz); δ5.91, 2H, S; δ6.42, 1H, S; δ7.03, 1H, S; δ7.16, 5H, S.

CC. (4-Methoxybenzyl)-3,4-methylenedioxy-6-(2-propenyl)benzene was prepared according to the following procedure:

Safrole (34.4 g), 4-methoxybenzyl alcohol (34.4 g), and oxalic acid (3 g) were refluxed in acetic acid (100 ml) and water (5 ml) for six hours. The oily product obtained on adding excess of water was extracted with ether, dried, and distilled to give a colorless oil, b.p. 165°-167° at 0.5 mm Hg (35 g) (Found: C, 76.8; H, 6.54, Calc. for $C_{18}H_{18}O_3$: C, 76.6; H, 6.43%); pmr spectrum: δ3.26, 2H, DT (J=7, 1.5 Hz); δ3.77, 3H, S; δ3.85, 2H, S; δ4.93, 1H, D of doublets (DD) (J=Q, 3, 1.5 Hz); δ5.07, DD (J=3, 1.5 Hz); δ5.81, 1H, M; δ5.88, 2H, S; δ6.58, 1H, S; δ6.67, 1H, S; δ6.80, 2H, D (J=9 Hz); δ7.02, 2H, D (J=9 Hz).

DD. (4-Methoxybenzyl)-3,4-methylenedioxy-6-n-propylbenzene was prepared by catalytic hydrogenation of CC in acetic acid in the presence of palladium charcoal. The product was a colorless oil, b.p. 169°-170° at 0.5 mm Hg (Found: C, 76.4; H, 7.16. Calc. for $C_{18}H_{20}O_3$: C, 76.0; H, 7.09%); pmr spectrum: δ0.92, 3H, T (J=Hz); δ1.51, 2H, M (J=7 Hz); δ2.50, 2H, T (J=7 Hz); δ3.77, 3H, S; δ3.86, 2H, S; δ5.86, 2H, S; δ6.55, 1H, S; δ6.67, 1H, S; δ6.80, 2H, D (J=9 Hz); δ7.02, 2H, D (J=9 Hz).

EE. (α-Vinylbenzyl)-3,4-methylenedioxy-6-methoxybenzene was obtained by methylation of (α-vinylbenzyl)-3,4-methylenedioxy-6-hydroxybenzene (Jurd, Tetrahedron, Vol. 29, pp. 2347-2353, 1973) as described in H above to give colorless needless from methanol, m.p. 92°-93° (Found: C, 76.1; H, 6.01%).

The above procedure was employed to prepare FF and GG.

FF. (α-Vinylbenzyl)-3,4-methylenedioxy-6-ethoxybenzene, colorless grains from methanol, m.p. 72°-73° (Found: C, 76.7, H, 6.45. Calc. for $C_{18}H_{18}O_3$: C, 76.6; H, 6.43%).

GG. (α-Vinylbenzyl)-3,4-methylenedioxy-6-n-propoxybenzene, colorless thick needles from methanol, m.p. 92°-93° (Found: C, 76.3; H, 6.15. Calc. for $C_{17}H_{16}O_3$: C, 76.1; H, 6.01%).

HH. (3-Methyl-4-methoxybenzyl)-3,4-methylenedioxybenzene was obtained as follows: Ortho-cresol (40 g) was refluxed with piperonyl alcohol (30 g) in 80% formic acid (100 ml) for 1.5 hours and diluted with water. Distillation of the oily product gave a fraction, b.p. 178°-180° at 0.5 mm Hg (34 g) which crystallized from benzene to give colorless needles, m.p. 95°; (Found: C, 74.3; H, 5.89. Calc. for $C_{15}H_{14}O_3$: C, 74.4; H, 5.83%); pmr spectrum: δ2.20, 3H, S; δ3.78, 2H, S; δ4.71, 1H, S; δ5.88, 2H, S; δ6.76, 6H, M.

The so-prepared phenol was methylated as described above in H yielding colorless needles from skelly solve F, m.p. 34°-35° (Found: C, 75.3; H, 6.43. Calc. for $C_{16}H_{16}O_3$: C, 75.0; H, 6.29%); pmr spectrum: δ2.17, 3H, S; δ3.74, 3H, S; δ3.76, 2H, S; δ5.80, 2H, S; δ6.86, 6H, M.

II. (3-Methyl-4-ethoxybenzyl)-3,4-methylenedioxybenzene was prepared as in HH. The product was a colorless oil, b.p. 165°-166° at 0.5 mm Hg; pmr spectrum: δ1.40, 3H, T (J=7 Hz); δ2.18, 3H, S; δ3.78, 2H, S; δ4.01, 2H, Q (J=7 Hz); δ5.88, 2H, S; δ6.80, 6H, M.

JJ. (3,5-Dimethyl-4-methoxybenzyl)-3,4-methylenedioxybenzene was obtained as follows: 2,6-dimethylphenol (48.8 g), piperonyl alcohol (60.8 g) and oxalic acid (2 g) were refluxed in acetic acid (100 ml) and water (10 ml) for 0.5 hours. Addition of water gave an oil which on distillation gave a fraction, b.p. 206°-208° at 0.5 mm Hg (72 g). This oil crystallized from benzene-skelly solve F to give colorless needles, m.p. 85°; (Found: C, 75.2; H, 6.40. Calc. for $C_{16}H_{16}O_3$: C, 75.0; H, 6.29%); pmr spectrum: δ2.18, 6H, S; δ3.74, 2H, S; δ4.48, 1H, S; δ5,87, 2H, S; δ6.69, 5H, M.

This phenolic product was methylated as in H above to give colorless needles from methanol, m.p. 44° (Found: C, 75.7; H, 6.68. Calc. for $C_{17}H_{18}O_3$: C, 75.5; H, 6.71%); pmr spectrum: δ2.24, 6H, S; δ3.69, 3H, S; δ3.76, 2H, S; δ5.88, 2H, S; δ6.63, 5H, M.

KK. Similarly, (3,5-dimethyl-4-methoxybenzyl)-3,4-methylenedioxybenzene was obtained as methanol, m.p. 49° (Found: C, 76.0, H, 7.09. Calc. for $C_{18}H_{20}O_3$: C, 76.0; H, 7.09%); pmr spectrum: δ1.39, 3H, T (J=7 Hz); δ2.23, 6H, S; δ3.81, 4H, M; δ5.88, 2H, S; δ6.73, 5H, M.

LL. (2,4-Dimethoxybenzyl)-3,4-methylenedioxybenzene was prepared according to the following procedure: A mixture of resorcinol (110 g) and piperonyl alcohol (76 g; 0.5 mol. equivalents) in 2% aqueous citric acid (1 liter) was refluxed for 15 hours and cooled. The crystalline product was recrystallized from benzene-skelly solve F to give colorless needles, m.p. 58°–59° (91 g) (Found: C, 68.8; H, 5.02. Calc. for $C_{14}H_{12}O_4$: C, 68.8; H, 4.95%); pmr spectrum: δ2.40, 1H, S (br); δ3.78, 2H, S; δ5.75, 1H, S (br); δ5.85, 2H, S; δ6.31, 2H, M; δ6.67, 3H, M; δ6.88, 1H, D (J=9 Hz).

The phenolic product was methylated as in H above to yield colorless, brittle prisms from skelly solve F, m.p. 51° (Found: C, 70.5; H, 5.90. Calc. for $C_{16}H_{16}O_4$: C, 70.6; H, 5.92%); pmr spectrum: δ3.78, 8H, S; δ5.88, 2H, S; δ6.40, 2H, M; δ6.70, 3H, S; δ6.69, 1H, D (J=9 Hz).

EXAMPLE 4

Synthesis of Group IV Compounds

MM. (3,4-Methylenedioxy-6-methoxybenzyl)-3,4-methylenedioxybenzene was prepared as follows: A solution of sesamol (13.4 g) and piperonyl alcohol (15.2 g) in 2% aqueous citric acid (250 ml) was refluxed for 2 hours and cooled. The oily product crystallized and was recrystallized from methanol to give colorless plates, m.p. 143° (Found: C, 66.2; H, 4.42. Calc. for $C_{15}H_{12}O_5$: C, 66.2; H, 4.44%); pmr spectrum: δ3.79, 2H, δ4.55, 1H, S; δ5.87, 2H, S; δ5.90, 2H, S; δ6.38, 1H, S; δ6.57, 1H, S; δ6.70, 3H, M.

Methylation of the so-produced phenol as in H above gave colorless needles from acetone-methanol, m.p. 106°–107° (Found: C, 67.0; H, 4.89. Calc. for $C_{16}H_{14}O_5$: C, 67.1; H, 4.93%); pmr spectrum: δ3.75, 3H, S; δ3.79, 2H, S; δ5.88, 2H, S; δ5.89, 2H, S; δ6.56, 1H, S; δ6.52, 1H, S; δ6.67, 3H, S.

NN. Similarly, (3,4-methylenedioxy-6-ethoxybenzyl)-3,4-methylenedioxybenzene was obtained as colorless needles from methanol, m.p. 44° (Found: C, 68.1; H, 5.29. Calc. for $C_{17}H_{16}O_5$: C, 68.0; H, 5.37%); pmr spectrum: δ1.36, 3H, T (J=7 Hz); δ3.79, 3H, S; δ3.92, 2H, Q (J=7 Hz); δ5.84, 2H, S; δ3.87, 2H, S; δ6.50, 1H, S; δ6.58, 1H, S; δ6.70, 3H, S.

EXAMPLE 5

Novel Synthesis of Group I Compounds 4,6-Di-t-butyl-2-(4-methoxybenzyl)phenol (C above) was prepared by heating a mixture of 2,4-di-t-butylphenol (41.2 g), 4-methoxybenzylalcohol (27.6 g) and toluene (5.0 ml) at 210°–220° C. in a flask fitted with a Dean-Stark trap filled with toluene. After 2 hours the reaction mixture was distilled under reduced pressure to give a pale yellow oil (57.6 g) which subsequently crystallized. The physical properties of the crystalline product were identical to that for the product in C above.

EXAMPLE 6

Anti-Procreant Tests with Group I Compounds

The compound to be tested was administered in a standard fly food containing 6 parts of sugar, 6 parts of powdered non-fat dry milk, and 1 part of powdered egg yolk. Treated food was prepared by mixing an appropriate amount of a solution or suspension of CBCP in acetone with a batch of the food. The acetone was evaporated (4–6 hours) and the dry material was repulverized.

Oviposition inhibition tests: Samples of treated food with a container of water were placed in cages containing 100 newly-emerged adult flies (family Muscidae). After the flies had been exposed to the treated diet for 6–7 days, ½ inch of moist standard fly larva-rearing medium (CSMA) in souffle cups was placed in the cages for oviposition. After 4–6 hours, the cup was removed and examined for eggs. If no eggs were laid, the medium was offered again at intervals of 1 or 2 days until it had been offered three times or the flies had oviposited.

Chemosterilancy tests: If eggs were laid in the above tests, the cups were filled with water and stirred to break up the egg masses. A random sample of 100 eggs from each cup was collected and placed on a small piece of black cloth which was then laid on top of moist larva-rearing medium in a rearing container. Observations were made to determine percentage of egg hatch and pupal development.

In those cases where the preliminary tests indicated that sterility had occurred in the flies fed the treated food, 10 males were removed from the test cage and crossed with 10 virgin, 4-day old, untreated females. These flies were maintained on untreated fly food. After 5 days, cups containing the larval-rearing medium was provided as previously described and a 100-egg sample was collected and place on moist larve-rearing medium. About a week after oviposition, examination was made to determine the percentage of hatched eggs and of pupae developed.

The results of the oviposition inhibition tests and the chemosterilancy tests are summarized below:

| Compound used | Amount in food (%) | Mortality, parent generation (%) | Oviposition | Egg hatch (%) | Pupal development (%) |
| --- | --- | --- | --- | --- | --- |
| C | 1.0 | 0 | None | — | — |
|  | 0.5 | 0 | None | — | — |
|  | 0.25* | 0 | Normal | 0 | 0 |
|  | 0.1 | 0 | " | 0 | 0 |
|  | 0.05 | 0 | " | 0 | 0 |
|  | 0.025 | 0 | " | 0 | 0 |
|  | 0.01 | 0 | " | 45 | 45 |
| A | 0.25 | 0 | " | 0 | 0 |
|  | 0.1 | 0 | " | 0 | 0 |
|  | 0.05 | 0 | " | 0 | 0 |
|  | 0.025 | 0 | " | 28 | 28 |
|  | 0.01 | 0 | " | 39 | 39 |
| B | 1.0 | 0 | " | 0 | 0 |
|  | 0.5 | 0 | " | 0 | 0 |
|  | 0.25 | 0 | " | 18 | 18 |
| D | 1.0* | 0 | " | 0 | 0 |
|  | 0.5 | 0 | " | 0 | 0 |
|  | 0.25 | 0 | " | 0 | 0 |
|  | 0.1 | 0 | " | 0 | 0 |
|  | 0.05 | 0 | " | 90 | 90 |
| None | 0 | 0 | Normal | 92–93 | 92–93 |

*100% sterilization of males at this concentration.

For purpose of comparison the above-described tests were applied to 2-benzyl-4-t-butylphenol and 2-(α-methylbenzyl)-4-t-butylphenol. The tests demonstrated that these compounds were ineffective in inducing sexual sterility or in inhibiting oviposition.

EXAMPLE 7

Anti-Procreant Tests with Group II Compound

The procedure outlined in Example 6 was followed using a Group II compound. The results are tabularized below.

| Compound used | Amount in food (%) | Mortality, parent generation (%) | Oviposition | Egg hatch (%) | Pupal development (%) |
|---|---|---|---|---|---|
| E | 1.0 | 0 | Normal | 0 | 0 |
|   | 0.5 | 0 | " | 0 | 0 |
|   | 0.25 | 0 | " | 0 | 0 |
|   | 0.1 | 0 | " | 36 | 36 |
| None | 0 | 0 | Normal | 92–93 | 92–93 |

For purposes of comparison the above-described tests were applied to 2,6-di-t-butyl-4-(4-methoxybenzyl) phenol and 2,6-di-t-butyl-4-(α-methyl-4-methoxybenzyl)-phenol, both compounds being ineffective in inducing sexual sterility or in inhibiting oviposition.

EXAMPLE 8

Anti-Procreant Tests with Group III Compounds

The procedure outlined in Example 6 was followed using Group III compounds. The results are summarized below:

| Compound used | Amount in food (%) | Mortality, parent generation (%) | Oviposition | Egg hatch (%) | Pupal development (%) |
|---|---|---|---|---|---|
| H | 0.025 | 0 | Normal | 45 | 45 |
|   | 0.01 | 0 | " | 14 | 14 |
| I | 1.0* | 0 | None | — | — |
|   | 0.025 | 0 | Normal | 38 | 38 |
|   | 0.01 | 0 | " | 63 | 63 |
| J | 0.01 | 0 | " | 2 | 2 |
|   | 0.05 | 0 | " | 3 | 3 |
|   | 0.025 | 0 | " | 61 | 61 |
|   | 0.01 | 0 | " | 30 | 30 |
| K | 1.0 | 0 | " | 0 | 0 |
|   | 0.5 | 0 | " | 0 | 0 |
|   | 0.25 | 0 | " | 0 | 0 |
|   | 0.1 | 0 | " | 70 | 70 |
| L | 0.25 | 60 | None | — | — |
|   | 0.1 | 0 | Normal | 0 | 0 |
|   | 0.05 | 0 | " | 0 | 0 |
|   | 0.01 | 0 | " | 91 | 91 |
| M | 0.1 | 0 | None | — | — |
|   | 0.05 | 0 | Normal | 0 | 0 |
|   | 0.025 | 0 | " | 0 | 0 |
|   | 0.01 | 0 | " | 19 | 19 |
| N | 0.25 | 75 | None | — | — |
|   | 0.1 | 0 | Normal | 0 | 0 |
|   | 0.05 | 0 | " | 33 | 33 |
| O | 0.5 | 80 | None | — | — |
|   | 0.25 | 0 | Normal | 0 | 0 |
|   | 0.05 | 0 | " | 48 | 48 |
| P | 0.5 | 0 | Normal | 0 | 0 |
|   | 0.25 | 0 | " | 0 | 0 |
|   | 0.1 | 0 | " | 10 | 10 |
|   | 0.05 | 0 | " | 36 | 36 |
| Q | 0.5 | 90 | None | — | — |
|   | 0.25 | 0 | Normal | 0 | 0 |
|   | 0.1 | 0 | " | 0 | 0 |
|   | 0.05 | 0 | " | 28 | 28 |
| R | 0.25 | 0 | " | 0 | 0 |
|   | 0.1 | 0 | " | 31 | 31 |
|   | 0.05 | 0 | " | 76 | 76 |
| S | 0.5 | 0 | " | 0 | 0 |
|   | 0.25 | 0 | " | 0 | 0 |
|   | 0.1 | 0 | " | 6 | 6 |
|   | 0.05 | 0 | " | 55 | 55 |
| T | 0.5 | 42 | " | 0 | 0 |
|   | 0.25 | 60 | " | 56 | 56 |
| U | 1.0 | 0 | " | 0 | 0 |
|   | 0.5 | 0 | " | 0 | 0 |
|   | 0.25 | 0 | " | 0 | 0 |
|   | 0.1 | 0 | " | 0 | 0 |
|   | 0.05 | 0 | " | 0 | 0 |
|   | 0.025 | 0 | " | 42 | 42 |
| V | 0.5 | 0 | " | 34 | 34 |
| CC | 0.25 | 50 | None | — | — |
|   | 0.1 | 0 | " | — | — |
|   | 0.05 | 0 | " | — | — |
|   | 0.025 | 0 | Normal | 0 | 0 |
|   | 0.01 | 0 | " | 15 | 15 |
| DD | 0.25 | 0 | None | — | — |
|   | 0.1 | 0 | Normal | 0 | 0 |
|   | 0.05 | 0 | " | 0 | 0 |
|   | 0.025 | 0 | " | 7 | 7 |
| HH | 0.25 | 80 | None | — | — |
|   | 0.1 | 0 | Normal | 82 | 82 |
| II | 0.5 | 80 | None | — | — |
|   | 0.25 | 0 | Normal | 50 | 50 |
| JJ | 0.5 | 70 | None | — | — |
|   | 0.25 | 0 | Normal | 0 | 0 |
|   | 0.1 | 0 | " | 6 | 6 |
|   | 0.05 | 0 | " | 70 | 70 |
| KK | 0.5 | 85 | None | — | — |
|   | 0.25 | 0 | Normal | 85 | 85 |
| LL | 0.25 | 60 | None | — | — |
|   | 0.1 | 0 | Normal | 76 | 76 |
| None | 0 | 0 | " | 92–93 | 92–93 |

*100% sterilization of males at this concentration.

For purposes of comparison the following compounds were tested and found to be ineffective in inducing sexual sterility or in inhibiting oviposition: 2-(4-methoxybenzyl)-3,4-methylenedioxyphenol, (α-methylbenzyl)-3,4-methylenedioxy-6-methoxybenzene, (α,α-dimethylbenzyl)-3,4-methylenedioxy-6-methoxybenzene, (α,α-dimethylbenzyl)-3,4-methylenedioxy-6-ethoxybenzene, (α,α-dimethylbenzyl)-3,4-methylenedioxy-6-n-propoxybenzene, (α,α-dimethylbenzyl)-3,4-methylenedioxy-6-n-butoxybenzene, (α,α-dimethylbenzyl)-3,4-methylenedioxy-6-n-pentoxybenzene, (α-vinylbenzyl)-3,4-methylenedioxy-6-methoxybenzene, (α-vinylbenzyl)-3,4-methylenedioxy-6-ethoxybenzene, (α-vinylbenzyl)-3,4-methylenedioxy-6-n-propoxybenzene.

EXAMPLE 9

Anti-Procreant Tests with Group IV Compound

The procedure outlined in Example 6 was followed substituting a Group IV compound for those of Group I. The table below provides a summary of results.

| Compound used | Amount in food (%) | Mortality, parent generation (%) | Oviposition | Egg hatch (%) | Pupal development (%) |
|---|---|---|---|---|---|
| NN | 0.1 | 0 | Normal | 0 | 0 |
|   | 0.05 | 0 | " | 2 | 2 |
| None | 0 | 0 | " | 92–93 | 92–93 |

(3,4-Methylenedioxy-6-methoxybenzyl)-3,4-methylenedioxybenzene was tested for purposes of comparison and was found to be ineffective in inducing sexual sterility or in inhibiting oviposition.

EXAMPLE 10

Growth-Inhibition Tests

The compound to be tested was added to one liter of water until the final concentration thereof was a growth-inhibiting amount. Fifty early fourth-stage larvae of the common malaria mosquito (Anopheles quadrimaculatus) were placed on this water. Larval food was administered daily. Dead larvae and pupae were removed, counted, and discarded daily. Live pupae were removed, rinsed, and transferred to a cup of distilled water. The cup was placed in an emergence cage, and the emerging adults, if any, were maintained on a sugar-water diet.

Two days after the last pupation, the pupal cups were observed for the number of dead pupae and the number of adults that were dead, unable to complete eclosion, or malformed. The effectiveness of the compound in inhibiting growth was determined by adding the number of dead larvae and pupae and the number of adults that were dead, unable to complete eclosion, and malformed. This sum was corrected by Abbott's formula (to adjust for the number of larvae or pupae which would die naturally) and designated as the GI (growth inhibition). The results are expressed as GI-90, i.e., the concentration of growth inhibitor in ppm that would prevent and/or retard growth in 90% of the treated larvae.

The results are summarized in the following table.

| Compound | GI-90 (ppm) |
|---|---|
| F | 0.042 |
| P | 0.047 |
| S | 0.036 |
| Q | 0.082 |
| A | 0.039 |
| K | 0.060 |
| I | 0.042 |
| J | 0.025 |
| V | 0.097 |
| E | 0.072 |
| JJ | 0.6 |
| KK | 0.9 |
| LL | 0.2 |
| O | 0.8 |
| CC | 0.2 |
| DD | 0.2 |
| T | 0.6 |
| W | 0.2 |
| H | 0.5 |
| U | 0.3 |

EXAMPLE 11

Anti-Procreant Tests on Screw-worm Fly

These tests were conducted on mass-reared screw-worm flies which had been obtained as pupae from the screwworm fly plant at Mission, Texas. The flies were held in cages with water and undiluted corn syrup in a colony room maintained at about 27° C. and 60% relative humidity (RH) with a 12-hour photoperiod beginning at 6 a.m. Adults that emerged were lightly anesthetized with $CO_2$ for ease of manipulation the same day.

The compounds tested (D, C, A, M, CC) all had low solubility in water, so the flies were offered the chemosterilants in a corn syrup mixture, the compounds being homogenized in the syrup by gradual mixing in a pestle and mortar. The mixtures obtained were fed to the flies in "Dixie" paper cups, 7 cm diameter, and rice hulls were placed on the surface of the food to prevent the flies from getting stuck in the viscous mixture.

Initially, varying concentrations of a chemosterilant were fed to the flies for the first 5 days of life. Thereafter, the chemosterilant was replaced with pure corn syrup. On the 7th day, 3 replicates of 10 flies were stimulated to oviposit and the flies which oviposited were checked for insemination by an examination of the spermathecae for live sperms. The total number of eggs per fly was estimated and the hatchability of these eggs (fertility) was determined 24 hours later (at 37° C.). Observations were made to determine percentage of egg hatch.

The results are summarized in the following table.

| Compound used | Amount in food (%) | Survival Male (%) | Survival Female (%) | Oviposition (%) | Inhibition of embryogenesis (%) |
|---|---|---|---|---|---|
| None |  | 50.0 | 81.3 | 83.3 | — |
| A | 0.01 | 54.0 | 71.3 | 63.3 | 100 |
|  | 0.10 | 47.0 | 68.0 | 90.0 | 100 |
| D | 0.01 | 46.0 | 49.3 | 66.7 | 95.2 |
|  | 0.10 | 55.0 | 88.7 | 95.0 | 100 |
| CC | 0.10 | 45.0 | 92.7 | 65.0 | 100 |
| M | 0.10 | 35.0 | 88.7 | 55.0 | 99.8 |
| C | 0.10 | 63.0 | 66.0 | 75.0 | 100 |

EXAMPLE 12

Mutagenicity and Toxicity Studies

The mutagenic activity of D, A, B, M, N, and CC were tested by the standard Ames' Salmonella/microsome procedure, which is reported to show better than 90% correlation with development of mammalian cancers (Ames et al., *Mutation Research*, Vol. 31, p. 347, 1975; McCann et al., *Proc. Nat. Acad. Sci.*, Vol. 72, p. 5135, 1975). Tester strains TA-100, TA-98, TA-1537 and the plate test method were used, employing concentrations of 10, 100, 1000, and 10,000 of compound per plate. The metabolic activation mixture (S-9 mix) used the 9000 times g supernatant of Arochlor-1254-induced rat liver homogenate at a level of 100 μl per ml of S-9 mix. The results indicate that in the strains tested compounds A, B, N, and CC are non-mutagenic, either without or with metabolic activation. Compounds D and M did exhibit revertant frequencies which exceeded the mean control value plus two or three standard deviations at doses between 10–10,000 μg/plate in TA-100 and S-9. This response is extremely weak relative to known mutagenic agents which revert this strain.

Compounds D, A, and B were also assayed for oral toxicity in mice. Estimated $LD_{50}$ for D, A, and B were 3430, 2510 and 3550 mg/kg body weight, respectively, indicating that these compounds are only slightly toxic.

Having thus described my invention, I claim:

1. A method of inhibiting procreation in insects, which comprises
   administering to the insects a compound selected from the group consisting of
   (a) compounds of the structure

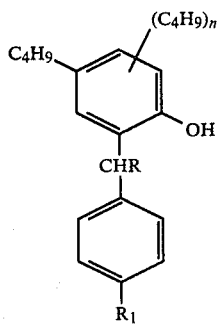

wherein n is an integer from 1 to 3,

R is hydrogen or lower alkyl containing from 1 to 6 carbon atoms, and $R_1$ is hydrogen, lower alkyl containing from 1 to 6 carbon atoms or lower alkoxy containing from 1 to 6 carbon atoms, (b) compounds of the structure

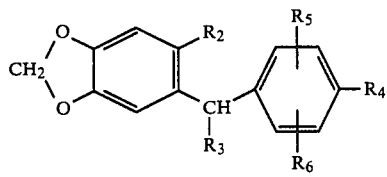

wherein $R_2$ is hydrogen, lower alkyl containing from 1 to 6 carbon atoms, lower alkoxy containing from 1 to 6 carbon atoms, or lower alkenyl containing from 2 to 6 carbon atoms, $R_3$ is hydrogen or lower alkyl containing from 1 to 6 carbon atoms, $R_4$, $R_5$, and $R_6$ are independently hydrogen, lower alkyl containing from 1 to 6 carbon atoms, and lower alkoxy containing from 1 to 6 carbon atoms, and wherein, if $R_2$ is hydrogen, then $R_5$ and $R_6$ must be independently lower alkyl containing from 1 to 6 carbon atoms or lower alkoxy containing from 1 to 6 carbon atoms, and wherein, if $R_4$, $R_5$, and $R_6$ are hydrogen and $R_3$ is methyl then $R_2$ must be lower alkoxy containing from 2 to 5 carbon atoms, (c) compounds of the structure

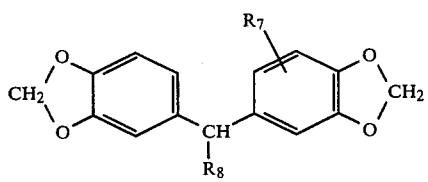

wherein $R_7$ is lower alkyl containing from 1 to 6 carbon atoms or lower alkoxy containing from 2 to 6 carbon atoms or lower alkenyl containing from 2 to 6 carbon atoms and $R_8$ is hydrogen or lower alkyl containing from 1 to 6 carbon atoms, and (d) compounds of the structure

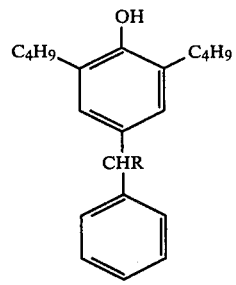

wherein

R is hydrogen or lower alkyl containing from 1 to 6 carbon atoms, said compound being administered in an amount insufficient to kill the insects but sufficient to inhibit procreation therein.

2. The method of claim 1 wherein the compound inhibits oviposition in insects thereby inhibiting procreation and the compound is administered in an amount sufficient to inhibit oviposition.

3. The method of claim 1 wherein the compound causes sexual sterility in insects thereby inhibiting procreation and the compound is administered in an amount sufficient to cause sexual sterility.

4. The method of claim 1 wherein the compound is 2,4-di-t-butyl-6-(4-methoxybenzyl) phenol.

5. The method of claim 1 wherein the compound is 2,4-di-t-butyl-6-(α-methylbenzyl) phenol.

6. The method of claim 1 wherein the compound is a (4-methoxybenzyl)-3,4-methylenedioxy-6-alkoxybenzene wherein the alkoxy group is methoxy, ethoxy, propoxy, butoxy, pentoxy, or hexoxy.

7. The method of claim 1 wherein the compound is an (α-methyl-4-methoxybenzyl)-3,4-methylenedioxy-6-alkoxybenzene wherein the alkoxy group is methoxy, ethoxy, propoxy, butoxy, pentoxy, or hexoxy.

8. The method of claim 1 wherein the compound is an (α-methylbenzyl)-3,4-methylenedioxy-6-alkoxybenzene wherein the alkoxy group is ethoxy, propoxy, butoxy, or pentoxy.

9. The method of claim 1 wherein the compound is a (4-methoxybenzyl)-3,4-methylenedioxy-6-alkenylbenzene wherein the alkenyl group is ethenyl, propenyl, butenyl, pentenyl, or hexenyl.

10. The method of claim 1 wherein the compound is a (4-methoxybenzyl)-3,4-methylenedioxy-6-alkylbenzene wherein the alkyl group is methyl, ethyl, propyl, butyl, pentyl, or hexyl.

11. The method of claim 1 wherein the compound is (3,4-methylenedioxy-6-ethoxybenzyl)-3,4-methylenedioxybenzene.

* * * * *

UNITED STATES PATENT AND TRADEMARK OFFICE
CERTIFICATE OF CORRECTION

PATENT NO. : 4,357,344
DATED : November 2, 1982
INVENTOR(S) : Leonard Jurd

It is certified that error appears in the above—identified patent and that said Letters Patent is hereby corrected as shown below:

Column 1, line 43, "progency" should be -- progeny --.

Column 3, line 40, "yound" should be -- young --.

Column 12, line 4, "8.47%" should be -- 9.47% --.

Column 12, line 17, "8.21" should be -- 9.21 --.

Column 17, line 31, after "2H," end of line, insert -- S; --.

Signed and Sealed this

Twenty-second Day of February 1983

[SEAL]

Attest:

Attesting Officer

GERALD J. MOSSINGHOFF

Commissioner of Patents and Trademarks